United States Patent [19]

Yoshida et al.

[11] Patent Number: 5,489,576
[45] Date of Patent: Feb. 6, 1996

[54] THERAPEUTIC AGENT FOR HEMORRHOIDAL DISEASES

[75] Inventors: Kenichi Yoshida, Ibaraki; Etsunosuke Noda, Yao, both of Japan

[73] Assignees: Senju Pharmaceutical Co., Ltd., Osaka; Amato Pharmaceutical Products, Ltd., Kyoto, both of Japan

[21] Appl. No.: 359,653

[22] Filed: Dec. 20, 1994

[30] Foreign Application Priority Data

Dec. 29, 1993 [JP] Japan .................... 5-351858

[51] Int. Cl.$^6$ .................. A61K 31/70; A61K 31/665
[52] U.S. Cl. ........................ 514/28; 514/100
[58] Field of Search ........................ 514/100, 28

[56] References Cited

U.S. PATENT DOCUMENTS

| 4,564,686 | 1/1986 | Ogata | 549/220 |
| 4,914,197 | 4/1990 | Yamamoto et al. | 536/117 |
| 4,948,786 | 8/1990 | Shimamoto et al. | 514/100 |

*Primary Examiner*—Jerome D. Goldberg
*Attorney, Agent, or Firm*—Wenderoth, Lind & Ponack

[57] ABSTRACT

A therapeutic agent for hemorrhoidal diseases, comprising, as an active ingredient, a diester phosphate compound of the formula (I)

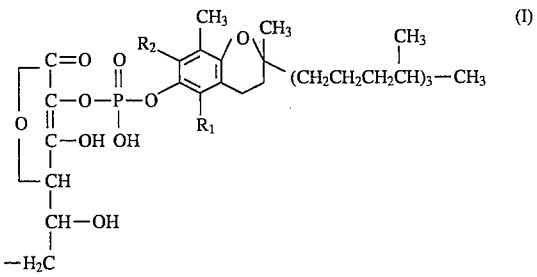

wherein $R_1$ and $R_2$ are the same or different and each is a hydrogen atom or a methyl, or a pharmacologically acceptable salt thereof, and a method for treating hemorrhoidal diseases, comprising administering a pharmaceutically effective amount of said diester phosphate compound or a pharmacologically acceptable salt thereof.

1 Claim, 1 Drawing Sheet

THERAPEUTIC AGENT FOR HEMORRHOIDAL DISEASES

FIELD OF THE INVENTION

The present invention relates to a novel pharmaceutical use of diester phosphate compounds. More particularly, the present invention relates to a use of a diester phosphate compound of ascorbic acid and tocopherol or a pharmacologically acceptable salt thereof as a therapeutic agent for hemorrhoidal diseases.

BACKGROUND OF THE INVENTION

Hemorrhoidal diseases include hemorrhoids, anal fissure and the like, and there have been conventionally marketed various preparations in diverse preparation forms, such as oral preparations and recto-anal preparations (e.g., suppository and ointment). Oral preparations intend to smooth dejection and alleviate congestion, bleeding, swelling and pain at the lesion.

In an attempt to give effects by direct application to the lesion, recto-anal preparations, such as suppositories and ointments, are used for decreasing pain, itchness, swelling, inflammation and bleeding at the lesion.

The pharmacological actions required of a therapeutic agent for hemorrhoidal diseases include the following actions on hemorrhoidal diseases, in other words, on the recto-anal region. They are antiedemic action, wound healing accelerating action, mucosal ulcer and inflammatory region healing action and microcirculation disorder improving action. The steroidal antiinflammatory agents generally used as therapeutic agents for hemorrhoids, such as hydrocortisone caproate and diflucortolon valerate, are superior in antiedemic action, whereas they retard wound healing in hemorrhoidal diseases. Moreover, a long-term, consecutive use of steroidal antiinflammatory agents or a use thereof in large amounts for the treatment of hemorrhoidal diseases results in various side effects such as hypersensitivity, irritation, degradation of adrenal and pituitary function, immunosuppression, retardation of systemic wound healing, increase of intraocular pressure and glaucoma. Accordingly, administration of steroidal antiinflammatory agents requires careful observation of the patients' conditions.

In view of the situation as described, a non-steroidal therapeutic agent for hemorrhoidal diseases, which is free of the above-mentioned problems and has antiedemic action, as well as wound healing accelerating action in hemorrhoidal diseases, has been studied for development.

SUMMARY OF THE INVENTION

The present inventors have now found that a diester phosphate compound of ascorbic acid and tocopherol and a pharmacologically acceptable salt thereof have superior therapeutic effects on hemorrhoidal diseases, and completed the present invention based on the new finding.

Accordingly, the present invention relates to a useful therapeutic agent for hemorrhoidal diseases, comprising, as an active ingredient, a diester phosphate compound of the formula (I)

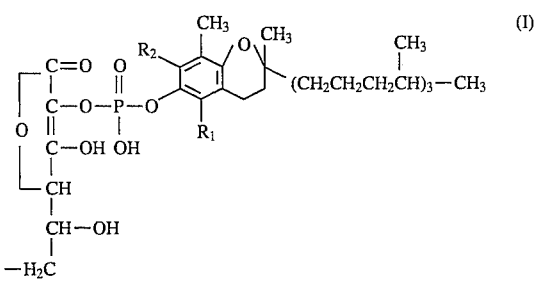

wherein $R_1$ and $R_2$ are the same or different and each is a hydrogen atom or a methyl, or a pharmacologically acceptable salt thereof [hereinafter said compound and a salt thereof are referred to as Compound (I)].

The present invention moreover relates to a method for treating hemorrhoidal diseases, comprising administering a pharmaceutically effective amount of a compound of the formula (I) or a pharmacologically acceptable salt thereof.

The present invention further relates to a use of a compound of the formula (I) or a pharmacologically acceptable salt thereof for producing a therapeutic agent for hemorrhoidal diseases.

BRIEF DESCRIPTION OF THE DRAWINGS

In FIG. 1, ○ is untreated group, □ is a group administered with a solvent, ● is a group administered with 5% EPC-K, ■ is a group administered with heparin sodium, ** indicates a significant difference of $p<0.01$ relative to the group administered with a solvent and ## indicates a significant difference of $p<0.01$ relative to the untreated group.

DETAILED DESCRIPTION OF THE INVENTION

Figure 1:
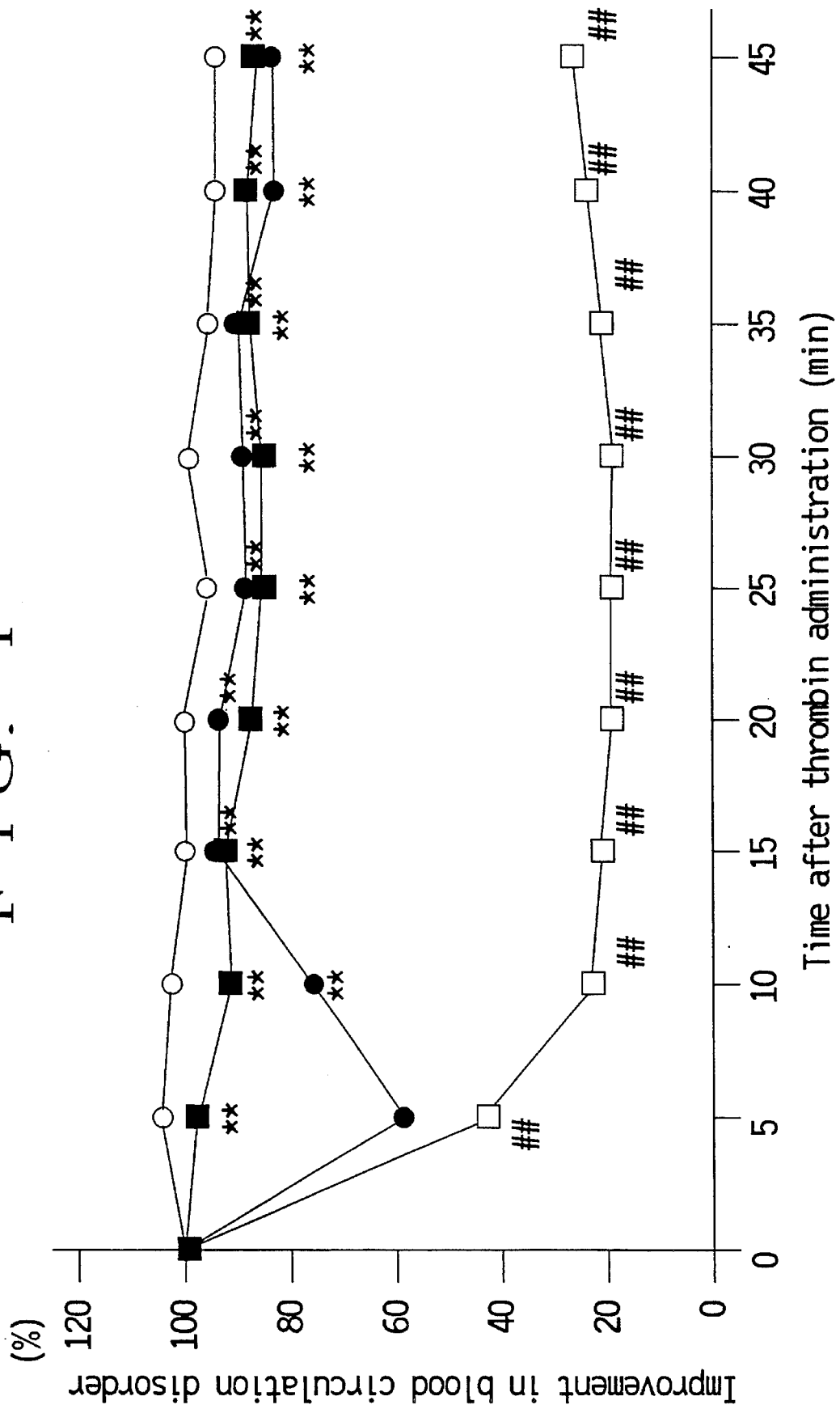
FIG. 1 is a graph showing improving action of Compound (I) on thrombin-induced rectal mucosa circulation disorder, wherein each value shows the mean±standard error (n=5).

The Compound (I) to be used for the treatment of hemorrhoidal diseases in the present invention is appropriately synthesized according to the method disclosed in, for example, U.S. Pat. Nos. 4,564,686 and 4,914,197, or an analogous method.

The Compound (I) to be used for the treatment of hemorrhoidal diseases in the present invention has been known to have various uses such as for an anticataract, an agent for the prevention and treatment of climacteric disturbance, cosmetics having beautifying action (U.S. Pat. No. 4,564,686) and an agent for the prevention and treatment of ischemic organ disorders (U.S. Pat. No. 4,948,786).

However, the usefulness of the Compound (I) as an ingredient of a therapeutic agent for hemorrhoidal diseases has not been reported.

The Compound (I) to be used for the treatment of hemorrhoidal diseases in the present invention can be used suitably for the treatment of various hemorrhoidal diseases, be it a free compound or a pharmacologically acceptable salt thereof. The pharmacologically acceptable salt thereof includes, for example, alkali metal salts such as sodium salt and potassium salt, and alkaline earth metal salts such as calcium salt and magnesium salt. Any salts other than these are usable insofar as they are pharmacologically acceptable.

The therapeutic agent for hemorrhoidal diseases of the present invention can contain one or more compounds of Compound (I) in combination, depending on the object and need.

The Compound (I) to be used for the treatment of hemorrhoidal diseases in the present invention shows extremely low toxicity and is superior in safety. Accordingly, it can be advantageously used for the treatment of hemorrhoidal diseases. For example, $LD_{50}$ of L-ascorbic acid DL-α-tocopheryl phosphate diester potassium salt (hereinafter abbreviated as EPC-K) is 5 g/kg or more for oral administration to rats and 100 mg/kg or more for intravenous injection to rats.

The Compound (I) can be administered orally or parenterally to mammals inclusive of human. When treating hemorrhoidal diseases, an oral preparation and a parenteral preparation may be used in combination according to the object and need. Examples of the oral preparation include tablets, capsules and granules. As a parenteral preparation, external preparations such as suppository, ointment, cream, liquid preparation and spray preparation are advantageously used. In case of ointments, which is one of the external preparations, they can be applied to the circumanal region or can show an extremely beneficial effect against hemorrhoidal diseases occurring in the recto-anus by inserting the ointment in the recto-anus upon housing same in an injectable container. These preparations can be prepared appropriately by known methods. Tablets, capsules and granules to be administered orally may comprise excipients such as starch and lactose, binders such as starch, dextrin, gum arabic, sodium carboxylmethylcellulose, carboxypropylmethylc ellulose and methylcellulose, and disintegrators such as calcium carboxymethylcellulose and crystalline cellulose. Where necessary, lubricants such as crystalline cellulose can be added. The suppositories may comprise a hard fat as the base material and emulsifiers such as glyceryl monostearate. The ointments may comprise a surfactant such as glyceryl monostearate, a suspending agent such as talc and light silicic anhydride, and a preservative such as methyl p-hydroxybenzoate, propyl p-hydroxybenzoate and butyl p-hydroxybenzoate, besides the ointment base material such as stearic acid, stearyl alcohol and petrolatum. The liquid preparations can contain a pH adjusting agent such as sodium hydrogenphosphate and citric acid, an isotonizing agent such as sodium chloride and potassium chloride, and a stabilizer such as sodium metabisulfite and acid sodium sulfite.

When Compound (I) is used for treating various hemorrhoidal diseases, the dose varies depending on the kind of Compound (I), body weight and age of patients, symptom to be treated, administration route etc. Generally, about 0.5–2 g (per application) from an about 0.1–25 w/w % ointment preparation is applied to the lesion or inserted into the recto-anus several times a day. In case of suppositories, Compound (I) is preferably contained by about 1–500 mg, preferably about 10–200 mg per suppository. In case of recto-anal preparations, a liquid preparation having a concentration of about 0.1–10 w/v % is preferably applied several times a day. In case of oral administration, Compound (I) is preferably administered in an amount of 10–1000 mg per dose for an adult several times a day.

The therapeutic agent for hemorrhoidal diseases of the present invention may comprise other therapeutic ingredients for hemorrhoidal diseases as appropriate, insofar as they do not impair the object of the present invention.

The present invention is described in more detail by illustrating Examples in the following.

EXAMPLE 1

Rectal Mucosa Irritating Action of Compound (I)

The rectal mucosa irritating action of Compound (I) was examined as in the following.

1. Animals used: Male Wistar rats weighing 135–200 g
2. Test substance: EPC-K added to an oil-in-water type cream
3. Test method:

The rats were fasted for 48 hours and the test substance was intrarectally administered. Five hours later, the rats were exsanguinated to death. The rectum was removed and the mucosa was visually observed. The condition of the mucosa was expressed in numerical units according to the evaluation standard shown in Table 1, and a central value and an average value were calculated, based on which the irritation by the test substance was classified according to the evaluation standard for irritation shown in Table 2.

TABLE 1

| Evaluation standard for mucosa | |
|---|---|
| Visual observation | value (irritation potency) |
| No abnormality | 0 |
| slight erythema difficult to define | 1 |
| light degree erythema | 2 |
| clear erythema and light degree edema but no necrosis | 3 |
| strong erythema and edema with necrosis | 4 |

TABLE 2

| Evaluation standard for irritation | |
|---|---|
| non-irritant substance | central value of irritation potency is 0 and average value is 0.4 or below |
| very light degree irritant substance | central value of irritation potency is 0.5 or 1 and average value is 0.5–1.4 |
| light degree irritant substance | central value of irritation potency is 1.5 or 2 and average value is 1.5–2.4 |
| medium degree irritant substance | central value of irritation potency is 2.5 or 3 and average value is 2.5–3.4 |
| highly irritant substance | central value of irritation potency is 3.5 or 4 and average value is 3.5 or above |

When the central value or average value was in between the two classes, an express ion exemplified by "very light-light degree irritant substance" is used.

4. Results

The results are shown in Table 3. As is evident from Table 3, Compound (I) did not exhibit any degree of irritation on the rectal mucosa.

TABLE 3

| Irritation of rectal mucosa by Compound (I) | | | |
|---|---|---|---|
| | Irritation potency | | |
| Group | Central value | Index value | Evaluation |
| untreated | 0 | 0.50 ± 0.34 | — |
| 5% EPC-K | 0 | 0.83 ± 0.54 | very light degree irritant substance |
| 1% EPC-K | 0 | 0.50 ± 0.34 | non-very light degree irritant substance |
| 0.2% EPC-K | 0 | 0.67 ± 0.42 | non-very light degree irritant substance |
| 8% citric acid cream | 1.5 | 1.17 ± 0.48 | very light-light degree irritant substance |

Note:
Index value is the mean ± standard error (n = 6).

EXAMPLE 2

Wound Healing Accelerating Effect of Compound (I) on Rectal Tissues

The wound healing accelerating effect of Compound (I) on rectal tissues was examined using the amount of hydroxyproline (Hyp) in tissue as an index.
1. Animals used: Male Wistar rats weighing 150–250 g
2. Test substance: EPC-K added to an oil-in-water cream to 1 w/w %
3. Test method:

The rats were fasted for 24 hours and a narrow saw was inserted in the rectum. A wound was made by two reciprocations of the saw in the rectum. The test substance was injected in the rectum once a day by 100 μl beginning immediately after forming of the wound. The rats were exsanguinated to death at 4 hours, 1, 3, 6 or 9 days thereafter and the rectum was removed. The removed rectum was delipidized, shredded and dried. After acid hydrolysis, pH was adjusted and hydroxyproline content was measured by the chloramine T oxidation method.
4. Results The results are shown in Table 4. As is evident from Table 4, Compound (I) showed earlier recovery of hydroxyproline content to normal value as compared with control group, without retarding mucosal healing 6 to 9 days later, thus suggesting the presence of wound healing accelerating effect of Compound (I) on the rectal tissues.

TABLE 4

| Group | Hydroxyproline content in rectal tissues (μg/mg) | | | | |
|---|---|---|---|---|---|
| | 4 hr later | 1 day later | 3 days later | 6 days later | 9 days later |
| Control | 19.67 | 19.69 | 23.46 | 25.63 | 27.38 |
| 1% EPC-K | 19.38 | 21.70 | 24.75 | 25.22 | 26.53 |

Each value is an average value (n=5). The Hyp content of normal rectum at 0 hour after the administration of Compound (I) was 22.26 μg/mg.

EXAMPLE 3

Effects of Compound (I) on Models with Hemorrhoidal Disease Induced by Croton Oil Mixture The suppressive effect of Compound (I) on recto-anal edema induced by a croton oil mixture was examined.
1. Animals used: Male Wistar rats weighing 140–250 g
2. Test substance: EPC-K added to petrolatum base material to 4 w/w %
3. Croton oil mixture Composition: distilled water:pyridine:diethyl ether:6% croton oil in diethyl ether solution=1:4:5:10

Preparation: Water and a small amount of diethyl ether were added to pyridine and mixed. Then, a 6% croton oil diethyl ether solution was added and the remaining diethyl ether was added thereto. The mixture was vigorously shaken.
4. Inducing inflammation A stype of a swab was impregnated with the croton oil mixture (160 μl) and the entire stype was inserted into the rectum for 10 seconds.
5. Determination of edema The test substance was administered intrarectally immediately after the induction of inflammation, and the anus was sealed for 4 hours with a clip so as to prevent leaking out of the substance.

At 24 hours after the induction of inflammation, the rats were exsanguinated to death and the weight of the recto-anal part, cut out in 15 mm length from 5 mm from the circular hairline on annal epithelium, was measured. The recto-anal coefficient ($RAC = Wra \cdot Wb^{-1} \cdot 10^3$) was calculated on the basis of the weight of the recto-anal part (Wra) and body weight (Wb) and used as an index of inflammation.
6. Results The results are shown in Table 5. As is evident from Table 5, the Compound (I) showed significant antiedemic action on the models with a hemorrhoidal disease induced by a croton oil mixture and was found to be useful as a therapeutic agent for hemorrhoidal diseases.

TABLE 5

Effects of Compound (I) on models with hemorrhoidal disease induced by croton oil mixture

| Group | Recto-anal coefficient (RAC) | Edema suppression (%) |
|---|---|---|
| untreated group | 0.67 ± 0.02 | — |
| control group with induced inflammation | 2.36 ± 0.06 | — |
| treated with 4% EPC-K | 2.03 ± 0.07* | 19.5* |

Note: Each value is the mean ± standard error (n = 10).

$$\text{Edema Suppression (\%)} = 100 - \left( \frac{\text{RAC of EPC-K administered group} - \text{RAC of untreated group}}{\text{RAC of control group} - \text{RAC of untreated group}} \right) \times 100$$

Note: significant difference from control group; *: $p < 0.05$

EXAMPLE 4

Improving Action of Compound (I) on Blood Circulation Disorder in Rectal Mucosa Blood circulation disorder improving action of Compound (I) was examined as in the following.
1. Animals used: Male Wistar rats weighing 140–250 g
2. Test substance: Physiological saline containing 5% EPC-K
3. Test method The rats were fasted for 18 hours and the test substance (1 ml) was intrarectally administered. The rat was fixed and the rectal mucosa was exposed. Then, the test substance (1 ml) was administered to the rectal mucosa, and bloodstream in the rectal mucosa was measured with a laser flowmeter. Thrombin was administered 30 minutes after the exposure of the mucosa, and bloodstream in the rectal mucosa was measured. As a positive control, a heparin sodium solution was used. Physiological saline was administered to a group to be administered with a solvent.
4. Results The results are shown in FIG. 1. As is evident from FIG. 1, the Compound (I) has an improving action on blood circulation disorder in hemorrhoidal diseases.

Formulation Example 1: Suppository

| EPC-K | 2 g |

| Formulation Example 1: Suppository | |
| --- | --- |
| Scopolia extract | 0.2 g |
| Tannic acid | 0.3 g |
| Ichthammol | 2 g |
| Ethyl aminobenzoate | 1 g |
| Cacao butter | suitable amount |

The above ingredients are formed into 10 suppositories by a known method.

| Formulation Example 2: Ointment | |
| --- | --- |
| L-Ascorbic acid DL-α-tocopheryl phosphate diester sodium salt (abbreviation EPC-NA) | 1 g |
| Propylene glycol | 1 ml |
| White petrolatum | suitable amount |
| total amount | 100 g |

The above ingredients are mixed by a known method to give an ointment.

| Formulation Example 3: External liquid preparation | |
| --- | --- |
| EPC-K | 3 g |
| Ethyl aminobenzoate | 1 g |
| Propylene glycol | 10 ml |
| Sterile purified water | suitable amount |
| Hydrochloric acid | suitable amount |
| Sodium hydroxide | suitable amount |
| total amount | 100 g |
| pH | 6.0 |

The above ingredients are dissolved by a known method and sterilized by filtration to give an external liquid preparation.

| Formulation Example 4: Oral preparation | |
| --- | --- |
| L-Ascorbic acid DL-α-tocopheryl phosphate diester calcium salt (abbreviation EPC-Ca) | 0.5 g |
| Lactose | 80 mg |
| Starch | 17 mg |
| Magnesium stearate | 3 mg |

The above ingredients are formulated into a tablet by a known method. If necessary, sugar coating may be applied.

The Compound (I) of the present invention has superior antiedemic action, wound healing accelerating action and blood circulation disorder improving action, and hardly shows irritation of rectal mucosa. Accordingly, the Compound (I) of the present invention is advantageously used for treating various hemorrhoidal diseases such as hemorrhoids and anal fissure. In addition, the therapeutic agent for hemorrhoidal diseases of the present invention can be used for a long time, since it shows no side effects observed in steroidal agents.

What is claimed is:

1. A method for treating hemorrhoidal diseases which comprises administering to a patient in need of such treatment, a pharmaceutically effective amount of a diester phosphate compound of the formula:

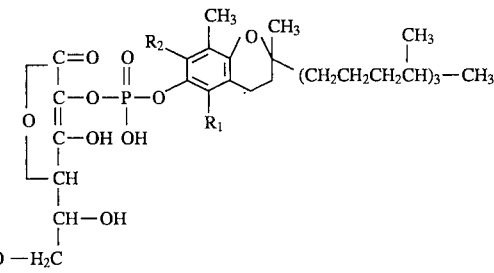

wherein $R_1$ and $R_2$ are the same or different and each is a hydrogen atom or a methyl, or a pharmacologically acceptable salt thereof.

* * * * *